(12) United States Patent
Sapin et al.

(10) Patent No.: US 10,299,979 B2
(45) Date of Patent: May 28, 2019

(54) UPPER LIMBS REHABILITATING, MONITORING AND/OR EVALUATING INTERACTIVE DEVICE

(71) Applicant: UNIVERSITÉ CATHOLIQUE DE LOUVAIN, Louvain-la-Neuve (BE)

(72) Inventors: Julien Sapin, Hannut (BE); Bruno Dehez, Liernu (BE)

(73) Assignee: UNIVERSITE CATHOLIQUE DE LOUVAIN, Louvain-la-Neuve (BE)

( * ) Notice: Subject to any disclaimer, the term of this patent is extended or adjusted under 35 U.S.C. 154(b) by 306 days.

(21) Appl. No.: 15/128,141

(22) PCT Filed: Mar. 26, 2015

(86) PCT No.: PCT/EP2015/056647
§ 371 (c)(1),
(2) Date: Sep. 22, 2016

(87) PCT Pub. No.: WO2015/144853
PCT Pub. Date: Oct. 1, 2015

(65) Prior Publication Data
US 2017/0095391 A1    Apr. 6, 2017

(30) Foreign Application Priority Data
Mar. 27, 2014    (EP) .................... 14162123

(51) Int. Cl.
*A61H 1/02*    (2006.01)
*A63B 71/06*   (2006.01)
(Continued)

(52) U.S. Cl.
CPC .......... *A61H 1/0274* (2013.01); *A61B 5/1124* (2013.01); *A61B 5/4064* (2013.01);
(Continued)

(58) Field of Classification Search
CPC .................... A61H 1/0274; A61H 1/02; A61H 2001/0203; A61H 2201/12;
(Continued)

(56) References Cited

U.S. PATENT DOCUMENTS

| | | |
|---|---|---|
| 5,466,213 A | 11/1995 | Hogan et al. |
| 5,830,160 A | 11/1998 | Reinkensmeyer |

(Continued)

FOREIGN PATENT DOCUMENTS

| | | |
|---|---|---|
| DE | 3048296 | 7/1982 |
| WO | 96/20643 | 7/1996 |
| WO | 2010/071252 | 6/2010 |

OTHER PUBLICATIONS

European Search Report dated Sep. 22, 2014 in corresponding European Application No. 14162123.5.

(Continued)

*Primary Examiner* — LaToya M Louis
(74) *Attorney, Agent, or Firm* — Wenderoth, Lind & Ponack, L.L.P.

(57) ABSTRACT

The present invention relates to a two-degree-of-freedom planar rehabilitating, monitoring and/or evaluating device comprising a first guiding mechanism (2), a second guiding mechanism (3), substantially parallel to the first guiding mechanism (2), a third guiding mechanism (4), substantially perpendicular to the first and second guiding mechanisms (2, 3), and an end-effector (5), wherein the third guiding mechanism (4) is connected to the first and second guiding mechanisms (2, 3), and wherein the end-effector (5) is connected to the third guiding mechanism (4). The present invention also relates to a two-degree-of-freedom planar rehabilitating, monitoring and/or evaluating interactive device adapted for rehabilitation, monitoring and/or assessment of the upper limbs of a subject, comprising said device.

16 Claims, 7 Drawing Sheets

(51) Int. Cl.
| | |
|---|---|
| *A63B 24/00* | (2006.01) |
| *A63B 21/00* | (2006.01) |
| *A63F 13/98* | (2014.01) |
| *A61B 5/11* | (2006.01) |
| *A61B 5/00* | (2006.01) |
| *A63F 13/25* | (2014.01) |
| *A63B 23/12* | (2006.01) |
| *A63B 21/005* | (2006.01) |
| *A63B 22/20* | (2006.01) |
| *A63B 22/00* | (2006.01) |
| *A63B 71/00* | (2006.01) |

(52) U.S. Cl.
CPC ........ *A61B 5/4833* (2013.01); *A63B 21/4035* (2015.10); *A63B 21/4045* (2015.10); *A63B 23/12* (2013.01); *A63B 24/0087* (2013.01); *A63B 71/0622* (2013.01); *A63F 13/25* (2014.09); *A63F 13/98* (2014.09); *A61H 2201/018* (2013.01); *A61H 2201/123* (2013.01); *A61H 2201/149* (2013.01); *A61H 2201/1635* (2013.01); *A61H 2201/1638* (2013.01); *A61H 2201/1666* (2013.01); *A61H 2201/5007* (2013.01); *A61H 2201/5043* (2013.01); *A61H 2201/5061* (2013.01); *A61H 2201/5064* (2013.01); *A63B 21/0058* (2013.01); *A63B 21/00178* (2013.01); *A63B 21/00181* (2013.01); *A63B 22/203* (2013.01); *A63B 23/1245* (2013.01); *A63B 23/1254* (2013.01); *A63B 2022/0094* (2013.01); *A63B 2024/0093* (2013.01); *A63B 2071/0072* (2013.01); *A63B 2071/0625* (2013.01); *A63B 2071/0638* (2013.01); *A63B 2220/13* (2013.01); *A63B 2220/51* (2013.01)

(58) Field of Classification Search
CPC .... A61H 2201/1253; A61H 2201/1261; A61H 2201/1269; A61H 2201/1276; A61H 2201/1635; A61H 2201/1638; A61H 2201/1664; A61H 2201/1666; A61H 2201/1671; A61H 2201/50; A61H 2201/5064; A61H 2201/5069; A61B 2505/09; A61B 5/1121; A61B 5/1124; A63B 23/12; A63B 21/154; A63B 21/0428; A63B 22/0015; A63B 22/0017
See application file for complete search history.

(56) References Cited

U.S. PATENT DOCUMENTS

| | | | |
|---|---|---|---|
| 8,613,715 B2* | 12/2013 | Wright | ..................... A61H 1/02 601/23 |
| 2003/0028130 A1 | 2/2003 | Wunderly et al. | |
| 2008/0000317 A1* | 1/2008 | Patton | .................. A61F 5/0102 74/500.5 |
| 2011/0132125 A1* | 6/2011 | Chen | ........................ B25J 9/023 74/473.21 |
| 2011/0300994 A1 | 12/2011 | Verkaaik et al. | |
| 2012/0109025 A1 | 5/2012 | Weinberg et al. | |
| 2013/0060171 A1 | 3/2013 | Fu et al. | |
| 2013/0210593 A1* | 8/2013 | McBride | .................. A63B 1/00 482/142 |
| 2014/0296750 A1* | 10/2014 | Einav | ..................... G06F 19/00 601/5 |

OTHER PUBLICATIONS

International Search Report dated May 28, 2015 in corresponding International Application No. PCT/EP2015/056647.
Gilliaux et al., "A robotic device as a sensitive quantitative tool to assess upper limb impairments in stroke patients: A preliminary prospective cohort study", J Rehabil Med, vol. 44, (2012), pp. 210-217.

* cited by examiner

UPPER LIMBS REHABILITATING, MONITORING AND/OR EVALUATING INTERACTIVE DEVICE

FIELD OF INVENTION

The present invention relates to the field of rehabilitation, especially upper limbs rehabilitation. More specifically, this invention relates to a two-degree-of-freedom planar interactive device adapted for upper limbs rehabilitation, monitoring and/or assessment of a subject.

BACKGROUND OF INVENTION

Stroke is a major cause of disability worldwide with approximately 800,000 new cases reported annually only in the United States, of which about 130,000 die. In the European Union stroke incidence appears to be markedly higher with over 460,000 deaths each year. The physical effects of stroke are variable and may include impairment in motor and sensory systems, language, perception, emotional and cognitive functions. Impairment of motor function usually involves paralysis or paresis of the muscles on the side of the body that is contralateral to the side of the brain lesion. People who have experienced a severe stroke often have significant impairment of muscle function of the arms, legs, and hands resulting in severe disability. Of all impairments that result from stroke, perhaps the most disabling is hemiparesis of the upper limbs. The upper limbs are of special concern because of the impact of upper extremity impairments on disability, independence, and quality of life. Consequently, improvement in motor abilities, and, more specifically, functional use of the upper extremity, is considered as one of the primary goals in post-stroke rehabilitation. However, even with rehabilitation, the functional recovery of arm and hand use is generally limited when compared with that of the lower extremities. Limited motor recovery in the paretic upper limb accounts indeed for a large share of the disabling sequels.

Traumatic brain injury as well as spinal cord injury require on-going, multiple disciplinary efforts to stabilize, decrease or prevent secondary impairments and complications and to improve or maintain social role functioning and quality of life for the individual throughout the remainder of the life. Because the average age at time of a spinal cord injury is 32, specialized care is necessarily long-term. Other types of diseases such as traumatic accidents and neurological disorders may result in similar deficiencies in strength, coordination and range of motion.

In order to recover or retain functional ability after a stroke or injury, patients undergo rehabilitation therapy, such as occupational and physical therapy.

Physical therapy with hands is still a main approach of therapy. However, the therapy with hands strongly relies on the physical therapist's personal experiences, and there is no means for accurately controlling the magnitude of applied force and the rotating extent of joint. Moreover one-to-one interaction between a therapist and a patient is limited in providing high intensity and high repetition training.

Robotic or interactive training is a new technology showing great potential for application in the field of neurorehabilitation. Robotic or interactive training has several advantages, e.g. adaptability, data collection, motivation, alleviation of patient safety concerns, and the ability to provide intensive individualized repetitive practice. Thus an objective of the present invention is to provide a device that may be used as a tool by a therapist whereby the therapist can assess the recovery of a patient and then utilize the present invention to assist the patient with the repetitive motions of the therapy.

Current robots usually show one degree of freedom or offer limited rehabilitation processes as they do not provide the range of motions needed for rehabilitation of multiple muscle groups.

U.S. Pat. No. 5,466,213 discloses an interactive robotic therapist which interacts with a patient to shape the motor skills. Said robotic therapist comprises a kinematic chain offering rotation/rotation movements. In use, said robot offers a limited rehabilitation surface—a 28 cm diameter circle only—due to its own kinematic chain.

US patent application 2012/0109025 relates to a robot for rehabilitation of the supination/pronation movements of the forearm and flexion/extension movements of the fingers. However, this device aims at rehabilitating complex movements such as grasping, and cannot be used as first-intention rehabilitation process.

According to the applicant, there is still a need for providing robots or interactive devices that can be used in first-intention rehabilitation processes and in later rehabilitation processes while also providing a large rehabilitation surface. Moreover, there is a need for providing an interactive device that can be used in rehabilitation as well as in quantitative assessment and monitoring.

Thus present invention aims at providing a large rectangular rehabilitation surface enabling full flexion/extension movements of the upper limbs (i.e. elbow and shoulder). To that end, the present invention comprises a H-shaped Cartesian coordinate planar interactive device including two motorized guiding mechanisms and one non-motorized guiding mechanism enabling, without interfering, motion of the limb of a subject through a large rehabilitation surface while minimizing the complexity, size, weight and cost of the interactive device.

Thus the present invention offers a large rehabilitation surface enabling rehabilitation and quantification of the patient recovery and progress thanks to an interactive device advantageously combining robotics and interactive environment to facilitate rehabilitation.

SUMMARY

This invention thus relates to a two-degree-of-freedom planar rehabilitating, monitoring and/or evaluating device, comprising a first guiding mechanism, a second guiding mechanism, substantially parallel to the first guiding mechanism, a third guiding mechanism, substantially perpendicular to the first and second guiding mechanisms, and an end-effector. According to one embodiment, the third guiding mechanism is connected to the first and second guiding mechanisms. According to one embodiment, the end-effector is connected to the third guiding mechanism.

According to one embodiment, the first guiding mechanism comprises at least one first guiding rail, a first slider slidably connected to the at least one first guiding rail and a first driving module driving the first slider; the second guiding mechanism comprises at least one second guiding rail, a second slider slidably connected to the at least one second guiding rail; the third guiding mechanism comprises at least one third guiding rail, a third slider slidably connected to the at least one third guiding rail and a third driving module driving the third slider. According to one embodiment, the third guiding mechanism is connected to the first and second guiding mechanisms through the first and second sliders. According to one embodiment, the second guiding mechanism does not comprise a driving module.

According to one embodiment, the end-effector is connected to the third slider.

According to one embodiment, the end-effector may be driven by the driving modules along a first axis defined by the at least one third guiding rail and along a second axis defined by the at least one first guiding rail.

According to one embodiment, the at least one first, second and/or third guiding rails allow a linear movement of the sliders whose amplitude extends to 2 meters, preferably to 1.5 meters, more preferably to 1 meter, even more preferably about 80 centimeters.

According to one embodiment, the second slider takes-up the torque induced by the force applied by a subject on the third guiding mechanism.

According to one embodiment, the second slider comprises a main body and at least one bearing part protruding downwards from the main body, wherein said at least one bearing part is slidably connected to the at least one second guiding rail and wherein the length, along the axis of the at least one second guiding rail, of said at least one bearing part between the two bearing points located at the opposite ends is at least 10 centimeters, preferably at least 20 centimeters, more preferably at least 30 centimeters.

According to one embodiment, the second slider comprises a main body and two bearing parts protruding downwards from the main body, wherein said first and second bearing parts are slidably connected to the at least one second guiding rail and wherein said first and second bearing parts are spaced, along the axis of the at least one second guiding rail, by at least 10 centimeters, preferably by at least 20 centimeters, more preferably by at least 30 centimeters.

According to one embodiment, the first and third sliders are connected respectively to the at least one first and third guiding rails through bearings, preferably through plain bearings; and the at least one bearing part of the second slider is connected to the at least one second guiding rail through bearings, preferably through ball bearings.

According to one embodiment, the device of the present invention also comprises a fourth guiding mechanism, substantially parallel to the first and second guiding mechanisms, a fifth guiding mechanism, substantially parallel to the third guiding mechanism and substantially perpendicular to the first, second and fourth guiding mechanisms and a second end-effector.

According to one embodiment, the fifth guiding mechanism is connected to the second and fourth guiding mechanisms. According to one embodiment, the second end-effector is connected to the fifth guiding mechanism.

According to one embodiment, the second guiding mechanism comprises two sliders: a first second slider and a second second slider.

According to one embodiment, the fourth guiding mechanism comprises at least one fourth guiding rail, a fourth slider slidably connected to the at least one fourth guiding rail and a fourth driving module driving the fourth slider; the fifth guiding mechanism comprises at least one fifth guiding rail, a fifth slider slidably connected to the at least one fifth guiding rail and a fifth driving module driving the fifth slider.

According to one embodiment, the fifth guiding mechanism is connected to the fourth and second guiding mechanisms through the fourth and second second sliders.

According to one embodiment, the second second slider takes up the torque induced by the force applied by a subject on the fifth guiding mechanism.

According to one embodiment, the second end-effector may be driven by the fourth and fifth driving modules.

The present invention also relates to a two-degree-of-freedom planar rehabilitation, monitoring and/or assessment interactive device adapted for rehabilitation, monitoring and/or assessment of the limbs, preferably the upper limbs, of a subject, comprising a two-degree-of-freedom planar rehabilitation device as described herein and a control system controlling the motion of said interactive device.

According to one embodiment, the device is arranged on a chassis and the interactive device comprises a display for interaction with the subject, a force sensor located in the end-effector and a position sensor located in the driving modules, and optionally a work plan.

According to one embodiment, the interactive device is able to be operated in three control modes defining the interaction between the subject and the interactive device: a passive mode, wherein the interactive device guides movements of a limb of the subject along a predefined path, an active mode, wherein the interactive device does not provide incentives to the subject and only controls the movements carried out by the subject and an activo-passive mode, wherein the interactive device assists the movement of a limb of the subject depending on the motor skills of the subject.

According to one embodiment, depending on the motor skills of the subject, the control system regulates in real-time the lateral interaction force, preventing the subject to deviate from a predefined path, the longitudinal interaction force, assisting the subject to move along the predefined path at a predefined speed, and the initiation time after which the interactive device initiates a movement if no movement has been started by the subject.

According to one embodiment, the interactive device further comprises user-friendly graphical environment displayed on the display and contextualized as tasks or games.

BRIEF DESCRIPTION OF THE DRAWINGS

FIG. 6A) axis of the end-effector according to an embodiment of the present invention.

FIG. 10A) of the handle, forearm support and hand support of the end-effector according to an embodiment of the present invention.

FIG. 10A) of the handle, forearm support and hand support of the end-effector according to an embodiment of the present invention.

REFERENCES

Figure 1:
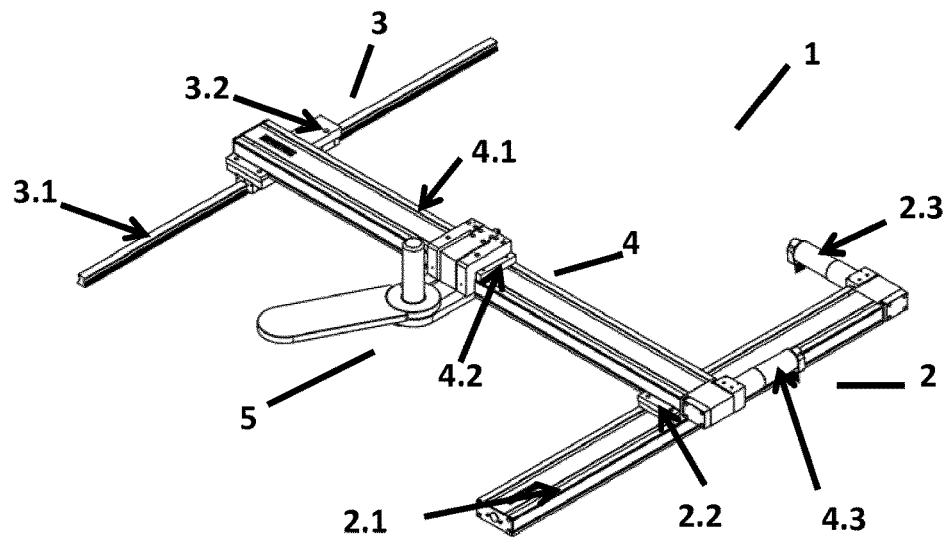
FIG. 1 is a perspective view of the rehabilitating, monitoring and/or evaluating device according to an embodiment of the present invention.

1 Device
2 First guiding mechanism
2.1 First guiding rail
2.2 First slider
2.3 First driving module
3 Second guiding mechanism
3.1 Second guiding rail
3.2 Second slider
3.3 Main body of the second slider
3.41 First bearing part of the second slider
3.42 Second bearing part of the second slider
4 Third guiding mechanism
4.1 Third guiding rail
4.2 Third slider
4.3 Third driving module
5 End-effector
5.1 Handle
5.11 Handle support
5.2 Hand support
5.21 Locking part
5.211 Oblong hole
5.212 Pear-shaped orifice
5.213 Half-pear-shaped orifice
5.22 Pin
5.23 Hole in the hand support designed for partly accommodating a rod of the handle support
5.24 Hole in the hand support designed for partly accommodating a rod of the forearm support
5.3 Sensor part
5.31 Space in the sensor part for accommodating a least one load cell
5.4 Stopper part
5.41 Stop
5.5 Forearm support
5.51 Rod of the forearm support
6 Interactive device
7 Display
8 Chassis
9 Protecting cover
10 Work plan
11 Device with two end-effectors
12 Fourth guiding mechanism
13 Fifth guiding mechanism
14 Second end-effector
16 Interactive device with two end-effectors
17 Frame
17.1 First support arm
17.2 Second support arm
17.3 Third support arm
17.4 Fourth support arm

Definitions

In the present invention, the following terms have the following meanings:

As used herein the singular forms "a", "an", and "the" include plural reference unless the context clearly dictates otherwise.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, more preferably of 5 percent.

The term "driving module" refers herein to any means enabling driving a slider along at least one guiding rail such as for instance a motor and a lead screw.

DETAILED DESCRIPTION

It should be understood that the spatial descriptions (e.g., "above", "below", "up", "down", "top", "bottom", "on", "under", etc.) made herein are for purposes of illustration only, and that devices of the present invention can be spatially arranged in any orientation or manner.

The present invention relates firstly to a two-degree-of-freedom planar device adapted for rehabilitation, monitoring and/or assessment of the limbs of a subject, preferably of the upper limbs of a subject.

Device

According to a first embodiment, the two-degree-of-freedom planar device has a H-shaped. Referring to the drawings, FIG. 1 illustrates said H-shaped device 1 comprising a first guiding mechanism 2, a second guiding mechanism 3, substantially parallel to the first guiding mechanism 2, and third guiding mechanism 4, substantially perpendicular to the first and second guiding mechanisms 2, 3.

According to one embodiment, the two-degree-of-freedom planar device 1 of the invention is a Cartesian coordinate device, i.e. a device whose two principal axes of control are linear (i.e. they move in a straight line and do not rotate) and are perpendicular to each other. Thus according to one embodiment, the two-degree-of-freedom planar device 1 does not provide rotation movement and the guiding mechanisms are not pivotably coupled between each other.

According to one embodiment, the first guiding mechanism 2 comprises at least one first guiding rail 2.1, a first slider 2.2 slidably connected to the at least one first guiding rail 2.1 and a first driving module 2.3 driving the first slider 2.2.

According to one embodiment, the second guiding mechanism 3 comprises at least one second guiding rail 3.1, a second slider 3.2 slidably connected to the at least one second guiding rail 3.1. According to one embodiment (not shown), the second guiding mechanism 3 comprises a second driving module driving the second slider 3.2.

Figure 2:
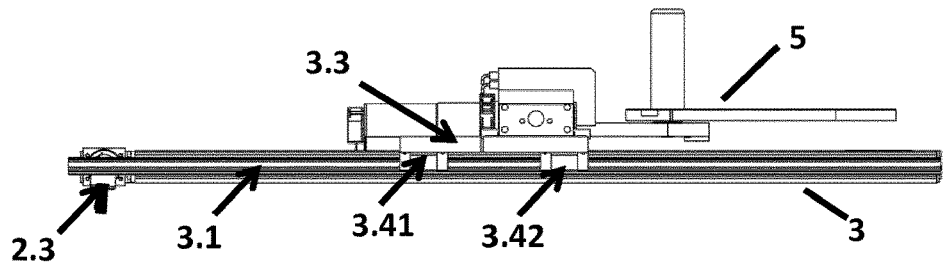
FIG. 2 is a side view of the rehabilitating, monitoring and/or evaluating device according to an embodiment of the present invention, from the side of the second guiding mechanism (i.e. the non-motorized guiding mechanism).

According to a preferred embodiment (as shown in FIGS. 1 and 2), the second guiding mechanism 3 does not comprise any driving module.

According to one embodiment, the third guiding mechanism 4 comprises at least one third guiding rail 4.1, a third slider 4.2 slidably connected to the at least one third guiding rail 4.1 and a third driving module 4.3 driving the third slider 4.2.

According to one embodiment, only two of the three guiding mechanisms comprise a driving module, preferably the second guiding mechanism 3 does not comprise a driving module. According to one embodiment, the two-degree-of-freedom planar device 1 of the invention comprises two active guiding mechanisms (i.e. comprising a driving module) and one passive guiding mechanism (i.e. without driving module).

According to one embodiment, the two-degree-of-freedom planar device 1 of the invention does not comprise three active guiding mechanisms.

According to one embodiment, the first, second, and/or third sliders 2.2, 3.2, 4.2 are slidably connected to respectively at least one first, second and/or third guiding rails 2.1, 3.1, 4.1. According to one embodiment, the first, second, and/or third sliders 2.2, 3.2, 4.2 are slidably connected to respectively two parallel first guiding rails 2.1, two parallel second guiding rails 3.1, and/or two parallel third guiding rails 4.1. According to a preferred embodiment, the first and third sliders 2.2, 4.2 are slidably connected to respectively two parallel first guiding rails 2.1 and two parallel third guiding rails 4.1 and the second slider 3.2 is slidably connected to one second guiding rail 3.1. According to one embodiment, the third guiding mechanism 4 substantially perpendicular to the first and second guiding mechanisms 2, 3 moves along a second or sagittal axis due to the first and second slider 2.2, 3.2; among said first and second slider 2.2, 3.2, only the first slider 2.2 is driven by a first driving module 2.3.

According to one embodiment, each of the first, second and third sliders 2.2, 3.2, 4.2 comprises at least one bearing slidably connected to the at least one first, second, and third guiding rail 2.1, 3.1 and 4.1. According to a preferred embodiment, the bearing is a plain bearing, a rolling element bearing such as for example a ball bearing, a fluid bearing or a magnetic bearing.

According to one embodiment, the first guiding mechanism 2 ensures linear movement of the first slider 2.2 along the at least one first guiding rail 2.1 defining a second axis (hereinafter referred to as the second or sagittal axis), through at least one standard bearing, such as those described hereabove. The first slider 2.2 may be driven by the first driving module 2.3.

According to one embodiment, the second guiding mechanism 3 ensures linear movement of the second slider 3.2 along the at least one second guiding rail 3.1 oriented along the second axis, through at least one standard bearing, such as those described hereabove. The second slider 3.2 may be indirectly driven due to movement of the third guiding mechanism 4 driven by the first driving module 2.3.

According to one embodiment, the third guiding mechanism 4 ensures linear movement of the third slider 4.2 along the at least one third guiding rail 4.1 defining a first axis (hereinafter referred to as the first or frontal axis), through at least one standard bearing, such as those described hereabove. The third slider 4.2 may be driven by the third driving module 4.3.

According to one embodiment, the first and second ends of the third guiding mechanism 4 are secured respectively to the first and second sliders 2.2, 3.2 by any means that one skilled in the art would find suitable such as for example screwing. Thus linear movement of the first slider 2.2 along the at least one first guiding rail 2.1 may ensure similar or identical linear movement of the second slider 3.2 along the at least one second guiding rail 3.1.

According to one embodiment, the at least one bearing of the first, second and third sliders 2.2, 3.2, 4.2 are the same or are different. According to a preferred embodiment, the first slider 2.2 comprises a plain bearing, the third slider 4.2 comprises a plain bearing and the second slider 3.2 comprises a ball bearing.

According to one embodiment, the at least one third guiding rail 4.1 allows a linear movement of the third slider 4.2 ranging from 0.1 centimeters to 2 meters, preferably from 10 centimeters to 1.5 meters, more preferably from 30 centimeters to 1 meter, even more preferably about 80 centimeters.

According to one embodiment, the at least one third guiding rail 4.1 allows a linear movement of the third slider 4.2 whose amplitude extends to 2 meters, preferably to 1.5 meters, more preferably to 1 meter, even more preferably about 80 centimeters.

According to one embodiment, the at least one and second guiding rails 2.1, 3.1 allow a linear movement of the first and second sliders 2.2, 3.2 ranging from 0.1 centimeters to 2 meters, preferably from 10 centimeters to 1.5 meters, more preferably from 30 centimeters to 1 meter, even more preferably about 80 centimeters.

According to one embodiment, the at least one and second guiding rails 2.1, 3.1 allow a linear movement of the first and second sliders 2.2, 3.2 whose amplitude extend to 2 meters, preferably to 1.5 meters, more preferably to 1 meter, even more preferably about 80 centimeters.

According to one embodiment, the H-shaped device 1 comprises an end-effector 5 secured to the third slider 4.2. Said end-effector may be slid or may be driven along the first axis due to the linear movement of the third slider 4.2 and along the second axis due to linear movement of the first and second sliders 2.2, 3.2. Thus said end-effector may be moved or may be driven along a rectangular rehabilitation surface; said movement being preferably achieved by only two motorized guiding mechanisms 2, 4 and one non-motorized guiding mechanism 3.

According to the applicant, without any second guiding mechanism 3, the transversal third guiding mechanism 4 may create, due to a moment arm which may be up to 2 meters long, an excessive torque, damaging the motorized first guiding mechanism 2.

Thus in order to ensure a large rectangular rehabilitation surface, a second guiding mechanism 3 has been implemented, leading to a H-shaped device. According to one embodiment, as illustrated in FIG. 2, the second guiding mechanism 3 comprises a slider 3.2 taking up the torque induced by the force applied by a subject on the end-effector 5 and thus on the third guiding mechanism 4, thereby avoiding the need of an additional driving module. According to said embodiment, the second slider 3.2 comprises a main body 3.3 and at least one bearing part protruding downwards from the main body 3.3. Said at least one bearing part is slidably connected to the at least one second guiding rail 3.1 by any standard bearing, such as those disclosed hereabove. According to one embodiment, the length of said at least one bearing part between the two bearing points located at the opposite ends, along the axis of the at least one second guiding rail 3.1, ranges from 10 centimeters to 100 centimeters, preferably from 20 centimeters to 80 centimeters, more preferably from 30 centimeters to 40 centimeters, thereby taking up the torque induced by the force created by the user. Said embodiment provides the holding of the perpendicularity between the second guiding mechanism 3 and the third guiding mechanism 4, and especially between the at least one second guiding rail 3.1 and the at least one third guiding rail 4.1.

According to a preferred embodiment, the second slider 3.2 comprises a main body 3.3 and two bearing parts 3.41, 3.42. Said first and second bearing parts 3.41, 3.42 protrude downwards from the main body 3.3. The first and second bearing parts 3.41, 3.42 are slidably connected to the at least one second guiding rail 3.1 by any standard bearing, such as those disclosed hereabove. According to one embodiment, the first and the second bearing part 3.41, 3.42 are securely spaced, along the axis of the at least one second guiding rail 3.1, by at least 10 centimeters, preferably by at least 20 centimeters, more preferably by at least 30 centimeters, thus taking up the torque induced by the force created by the user. Preferably the first and the second bearing part 3.41, 3.42 are securely spaced, along the axis of the at least one second guiding rail 3.1, by a length ranging from 10 centimeters to 100 centimeters, preferably from 20 centimeters to 80 centimeters, more preferably from 30 centimeters to 40 centimeters, thus taking up the torque induced by the force created by the user. Said embodiments provide the holding of the perpendicularity between the second guiding mechanism 3 and the third guiding mechanism 4, and especially between the at least one second guiding rail 3.1 and the at least one third guiding rail 4.1.

Figure 13A:
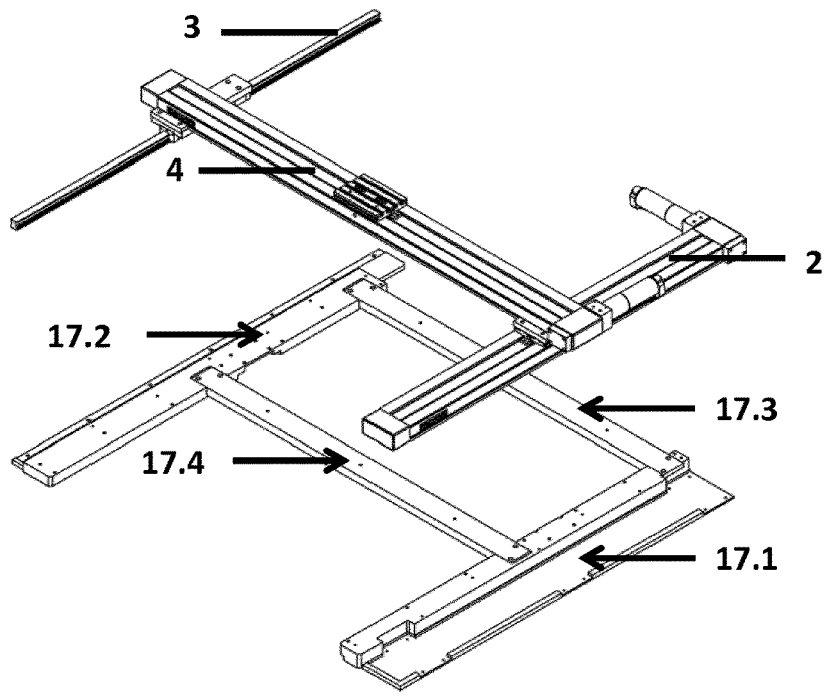
FIG. 13A is an exploded view of a frame and the rehabilitating, monitoring and/or evaluating device according to an embodiment of the present invention.
Figure 13B:
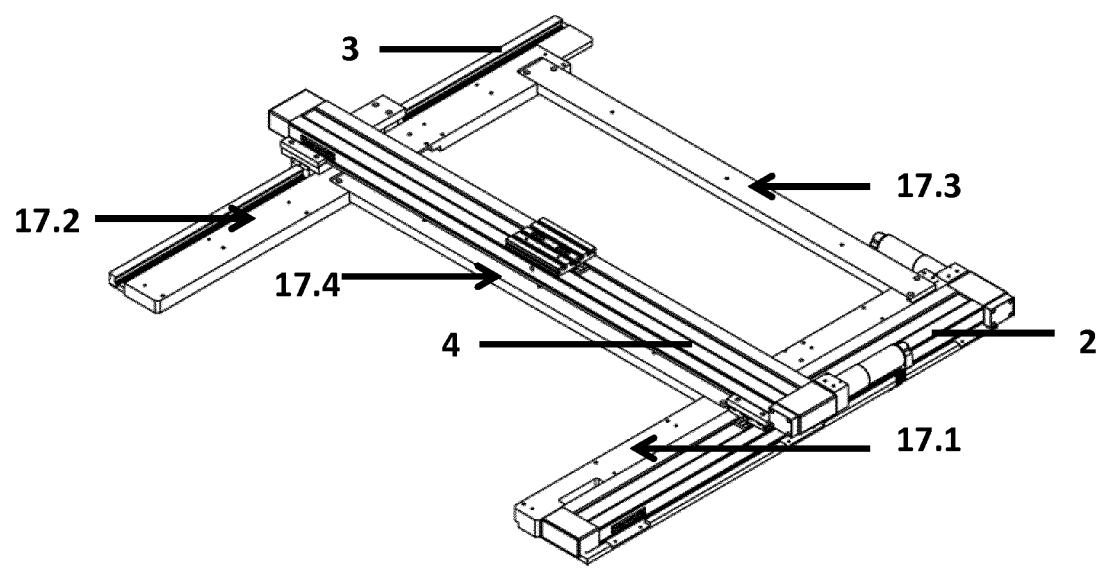
FIG. 13B is a perspective view of the rehabilitating, monitoring and/or evaluating device fixed on a frame according to one embodiment of the present invention.

According to one embodiment, as depicted in FIGS. 13A and 13B, the two-degree-of-freedom planar device 1 is fixed on a frame 17 in order to maintain and improve the parallelism of the first and second guiding mechanism 2, 3. According to one embodiment, the frame comprises a first, second, third and a fourth support arm 17.1, 17.2, 17.3 and 17.4 arranged such that the first and second support arms 17.1 and 17.2 are substantially parallel between each other and such that the third and fourth support arms 17.3 and 17.4 are substantially parallel between each other and substantially perpendicular to the first and second support arms 17.1 and 17.2. According to one embodiment, the third and fourth support arms 17.3 and 17.4 are each connected to the first and second support arms 17.1 and 17.2. According to one embodiment, the first, second and third support arms 17.1, 17.2 and 17.3 form a U-shaped frame and the fourth support arm 17.4 is located perpendicularly between the two ends of the first and second support arms 17.1 and 17.2. According to one embodiment, in order to avoid interfering with the subject, the fourth support arm 17.4 is not located at an end of the first and second support arm 17.1 and 17.2. According to one embodiment, the fourth support arm 17.4 is located about the middle of the first and second support arm 17.1 and 17.2.

According to one embodiment, the first guiding module 2, especially the first guiding rail 2.1 is fixed to the first support arm 17.1 and the second guiding mechanism 3, especially the second guiding rail 3.1 is fixed to the second support arm 17.2.

Interactive Device

The present invention also relates to a two-degree-of-freedom planar interactive device, adapted for assisted rehabilitation, quantitative assessment and/or monitoring performance evolution of the limbs of a subject, preferably of the upper limbs of a subject. In one embodiment, interactive device and robot have the same meaning. In one embodiment, assessment and evaluation have the same meaning.

Figure 3:
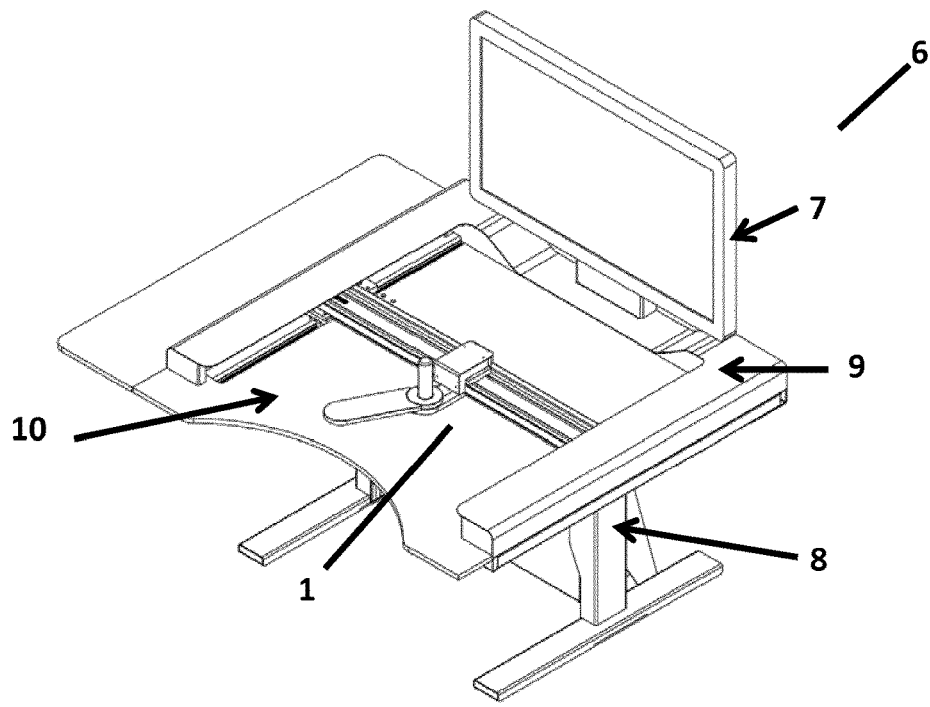
FIG. 3 is a perspective view of the rehabilitating, monitoring and/or evaluating interactive device according to an embodiment of the present invention.

According to one embodiment, as illustrated in FIG. 3, the assisted rehabilitation, quantitative assessment and/or monitoring interactive device 6 comprises the device 1 as described hereabove.

Referring again to FIG. 3, the rehabilitating, monitoring and/or evaluating interactive device 6 generally comprises a control system controlling the motion of the interactive device. According to one embodiment, the control system controls the motion of the interactive device 6 and is connected to the first and third driving modules 2.3, 4.3 of respectively the first and third guiding mechanism 2, 4. According to one embodiment, said control system is parameterized by a computer intended to be used by the therapist (not shown in FIG. 3). According to one embodiment, at it is well known from those skilled in the art, the control system comprises memory for storing data and a processor for calculating parameters changes depending on the interactive device-patient interaction and the therapist instructions.

According to one embodiment, the interactive device 6 is arranged on a chassis 8 adjustable in height and holding the alignment of the guiding mechanisms during use. According to one embodiment, the interactive device 6 further comprises a display interface for control by the physiotherapist (not shown), and a display for immersion of the subject in the therapy 7, such as for example a screen or a head-mounted display (not shown). According to one embodiment, thanks to the display 7 a graphical user interface (GUI) creates a user-friendly environment contextualized as task or game.

According to one embodiment, the interactive device 6 further comprises a work plan 10 preventing the view by the subject to its lower limbs. According to one embodiment, the work plan 10 is located under the third guiding mechanism 4 (cf. FIG. 3). According to one embodiment wherein the interactive device comprises two end-effectors, the work plan 10 is located under the first, second and fourth guiding mechanism 2, 3, 12 (cf. FIG. 5). According to one embodiment, the interactive device 6 further comprises a protecting cover 9 which protects the first and second guiding mechanism 2, 3 while also preventing physical harm to any subject and/or operator. According to one embodiment, the interactive device 6 also comprises a sound system for enhancing the feeling of immersion of the subject in the therapy.

According to one embodiment, the interactive device 6 comprises sensors connected to the control system. According to one embodiment, the position, velocity and/or force of the two degrees of freedom of the interactive device 6 are measured by standard off-the-shelf components. According to one embodiment, the end-effector 5 comprises a force sensor intended to measure the interaction force between the subject and the interactive device. According to one embodiment, each driving modules 2.3, 4.3 comprise a position sensor measuring the kinematics of the subject's limb. According to one embodiment, the two-degree-of-freedom planar interactive device 6 provides a feedback loop.

According to one embodiment, the interactive device 6 comprises a detection system shutting down the interactive device if a portion of the body of the subject, other than a single forearm, crosses the rehabilitation surface, thereby providing a safety feature.

Method of Use

The present invention also relates to a method of use of the interactive device 6.

According to one embodiment, before any use of the interactive device 6, all subjects are installed in an ergonomic and standardized sitting or standing position in order to minimize compensatory movements. According to one embodiment, if the shoulder of the subject is too weak, the forearm of the patient is secured to a forearm support associated with an orthosis. According to one embodiment, if the hand of the subject is too weak, the hand is secured to the handle or the handle may be removed. According to one embodiment, depending on the spasticity of the subject, various handle are implemented.

According to one embodiment, the control system uses input data from the sensors to drive an icon, cursor or other figure graphically on the display 7. Interactive games, such as maze games, controlled by the control system and using artificial intelligence to react to subject input, may be used to ensure immersion of the subject in the therapy. The display 7 provides a visual, interactive gaming environment for performing therapeutic exercises using the interactive device 6 and especially the end-effector 5. According to one embodiment, the control system provides real-time feedback, advantageously motivating the subject to perform tasks.

According to one embodiment, the interactive device 6 comprises three operating modes.

According to a first embodiment, the present interactive device 6 is implemented in an assisted rehabilitation operating mode. In said embodiment, the interactive device enables a subject to perform repetitive tasks in a motivating environment.

According to a second embodiment, the present interactive device 6 is implemented in a quantitative assessment operating mode. In said embodiment, said interactive device uses kinematic measures to assess or evaluate upper limbs quantitatively and objectively. Kinematics indices may be computed from various tasks performed by the subjects.

According to a third embodiment, the present interactive device 6 is implemented in a monitoring operating mode. In said embodiment, the monitoring of the performance evolution of a subject, either during assisted rehabilitation or during quantitative assessment is achieved. During each task or exercise, for each patient, specific parameters may be recorded: the number of performed movements, the mean longitudinal interaction force, the mean lateral interaction force, the mean speed and the mean time of initiation. Each parameter may be compared to reference parameters obtained by healthy subject.

According to one embodiment, the tasks are selected from single discrete tasks consisting in reaching a target in the most precise and direct manner, complex discrete tasks consisting in reaching target through a predefined path or rhythmic and cyclic tasks consisting in performing continuous cyclic tasks.

According to one embodiment, the interactive device 6 is able to operate in several control modes that define the interaction between the subject, the interactive device, and the therapist, namely a passive mode, an active mode and an activo-passive mode.

According to one embodiment, in the active mode, the interactive device 6 does not provide incentives to the subject and only controls and records the movements accomplished by the subject. According to one embodiment, in the passive mode, the interactive device 6 guides the movements of the end-effector and thereby of the limb, preferably through the hand and/or forearm, of the subject along a predefined path depending on the selected task. According to one embodiment, in the activo-passive mode, the interactive device 6 assists the movement of the limb, preferably through the hand and/or forearm, of the subject depending on the motor skills of the subject.

Moreover, during each task, the assistance is adjusted in real-time by the control system depending on the motor skills of the subject.

Figure 12:
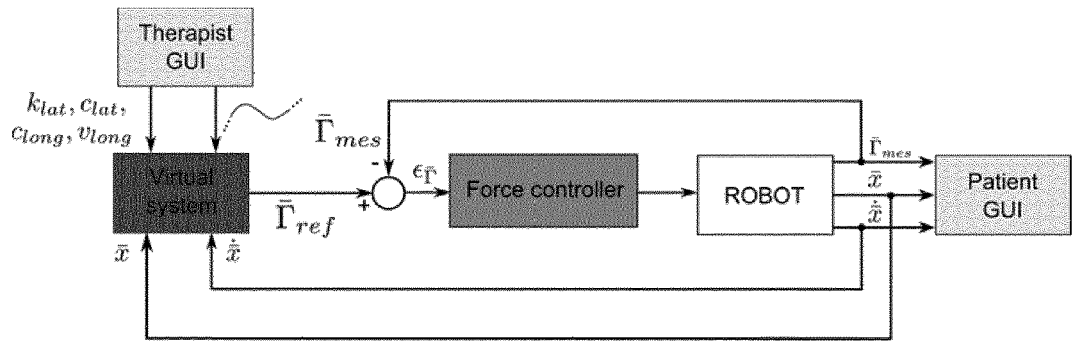
FIG. 12 is a flow chart of a control strategy according to an embodiment of the present invention.

According to one embodiment, the control strategy of the control system, as depicted in FIG. 12, ensures control of the force interaction between the interactive device and the subject. The control system comprises a virtual system, directed by the therapist through the therapist GUI, which regulates the force controller which again regulates the interactive device. According to one embodiment, the virtual system regulates four parameters, namely the longitudinal interaction force, the lateral interaction force, the reference speed and initiation time.

According to one embodiment, the lateral interaction force applied by the interactive device prevents, through motive or resistive forces, the subject to deviate from the predefined path. According to one embodiment, the longitudinal interaction force applied by the interactive device guides or assists, through motive or resistive forces, the subject to follow or move along the predefined path at a predefined speed: the reference speed. According to one embodiment, the control system initiates, through motive force, a movement if the subject has not started by itself any movement after a predefined time of initiation. According to one embodiment, the longitudinal interaction force, the lateral interaction force, the reference speed and the time of initiation are evolving during a task or during an exercise comprising repetitive tasks. Evolution of the parameters is achieved in real-time either for helping, by increasing assistance, the subject to perform the predefined task or for challenging the subject by reducing the assistance.

According to one embodiment, the interactive device 6 provides feedbacks to the subjects, such as visual feedbacks, auditory feedback, sensorimotor feedback or also quantitative feedbacks by computing performance indicia in real-time during use.

According to one embodiment, the interactive device 6 is used in first-intention rehabilitation processes and in later rehabilitation processes.

According to a preferred embodiment, the subject is a post-stroke or post traumatic brain patient, in acute or sub-acute phase or cerebral palsy children.

Device with Two End-Effectors and Associated Interactive Device

Figure 4:
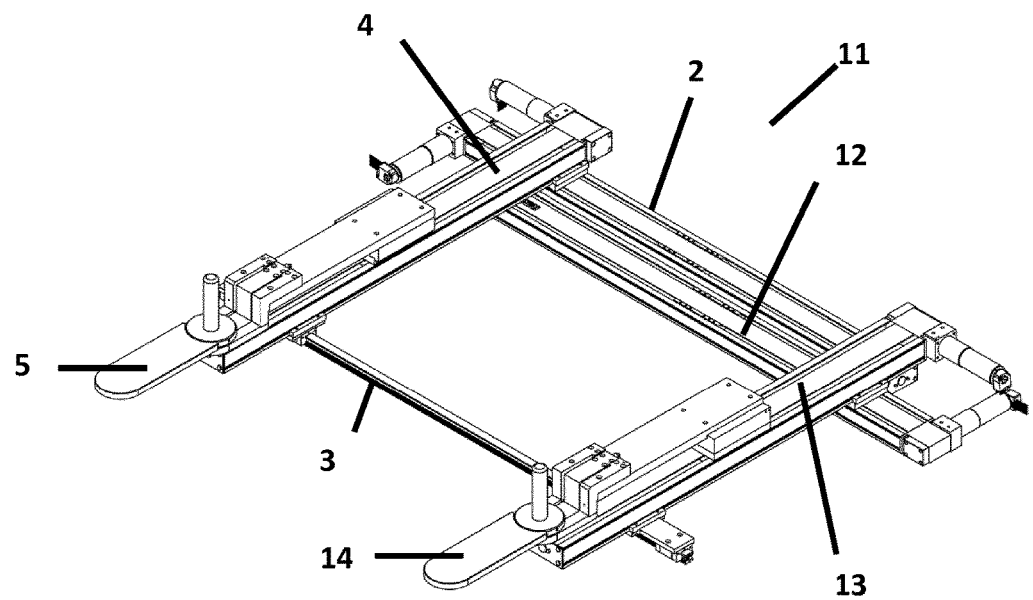
FIG. 4 is a perspective view of the rehabilitating, monitoring and/or evaluating device according to another embodiment of the present invention.
Figure 5:
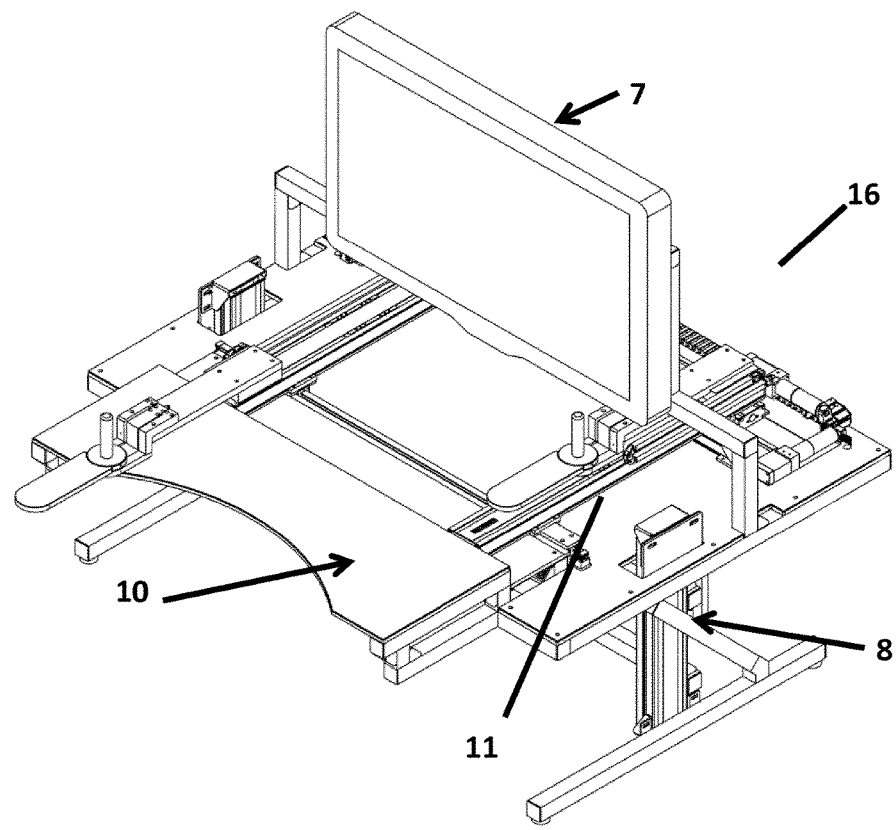
FIG. 5 is a perspective view of the rehabilitating, monitoring and/or evaluating interactive device according to another embodiment of the present invention.

According to an alternative embodiment, the device of the present invention also comprises two end-effectors. In said embodiment, as depicted in FIGS. 4 and 5, the device with two end-effectors comprises two of the devices as described hereabove. Said two devices are arranged such that the third guiding mechanism of each of said two devices are parallels and such that the first guiding mechanism of each of said two devices abut against each other. In said embodiment, the device with two end-effectors comprises only one second guiding mechanism shared by the two devices and connected to the third guiding mechanism of each of said two devices.

In other word, as illustrated in FIG. 4, the device 11 with two end effectors may comprise a device 1 as described hereabove and further comprises a fourth guiding mechanism 12 substantially parallel to the first and second guiding mechanisms 2, 3, a fifth guiding mechanism 13, substantially parallel to the third guiding mechanism 4 and substantially perpendicular to the first, second and fourth guiding mechanisms 2, 3, 12, and a second end-effector 14. According to one embodiment, the fifth guiding mechanism 13 is connected to the second and fourth guiding mechanisms 4, 12. According to one embodiment, the end-effector 14 is connected to the fifth guiding mechanism 13.

According to one embodiment, the second guiding mechanism 3 comprises two sliders. According to one embodiment, the second guiding mechanism 3 does not comprise a driving module.

According to one embodiment, the fourth guiding mechanism 12 comprises at least one fourth guiding rail, a fourth slider slidably connected to the at least one fourth guiding rail and a fourth driving module driving the fourth slider.

According to one embodiment, the fifth guiding mechanism 13 comprises at least one fifth guiding rail, a fifth slider slidably connected to the at least one fifth guiding rail and a fifth driving module driving the fifth slider.

According to one embodiment, the fifth guiding mechanism 13 is connected to the fourth and second guiding mechanisms 12, 3 through the fourth and the second second sliders.

According to one embodiment, the second second slider takes up the torque induced by the force applied by a subject on the fifth guiding mechanism 13.

According to one embodiment, the end-effector 14 is driven by the fourth and fifth driving modules.

According to one embodiment, the fourth, fifth, and/or second second sliders are slidably connected to respectively at least one fourth, fifth and second guiding rails. According to one embodiment, the fourth, fifth, and/or second second sliders are slidably connected to respectively two parallel fourth guiding rails, two parallel fifth guiding rails, and/or two parallel second guiding rails. According to a preferred embodiment, the fourth and fifth sliders are slidably connected to respectively two parallel fourth guiding rails and two parallel fifth guiding rails and the second second slider is slidably connected to one second guiding rail.

According to one embodiment, each of the fourth, fifth, and second second sliders comprises at least one bearing slidably connected to the at least one fourth, fifth, and second guiding rail. According to a preferred embodiment, the bearing is a plain bearing, a rolling element bearing, such as for example a ball bearing, a fluid bearing or a magnetic bearing.

According to one embodiment, the fourth guiding mechanism 12 ensures linear movement of the fourth slider along the at least one fourth guiding rail, through at least one standard bearing, such as those described hereabove. The fourth slider may be driven by the fourth driving module.

According to one embodiment, the fifth guiding mechanism 13 ensures linear movement of the fifth slider along the at least one fifth guiding rail, through at least one standard bearing, such as those described hereabove. The fifth slider may be driven by the fifth driving module.

According to one embodiment, the at least one bearing of the fourth, fifth and second second sliders are the same or are different. According to a preferred embodiment, the fourth slider comprises a plain bearing, the fifth slider comprises a plain bearing and the second second slider comprises a ball bearing.

According to one embodiment, the at least one fourth guiding rail allows a linear movement of the fourth slider ranging from 0.1 centimeters to 2 meters, preferably from 10 centimeters to 1.5 meters, more preferably from 30 centimeters to 1 meter, even more preferably about 80 centimeters.

According to one embodiment, the at least one fourth guiding rail allows a linear movement of the fourth slider whose amplitude extends to 2 meters, preferably to 1.5 meters, more preferably to 1 meter, even more preferably about 80 centimeters.

According to one embodiment, the at least one fifth guiding rail allows a linear movement of the fifth slider ranging from 0.1 centimeters to 2 meters, preferably from 10 centimeters to 1.5 meters, more preferably from 30 centimeters to 1 meter, even more preferably about 80 centimeters.

According to one embodiment, the at least one fifth guiding rail allows a linear movement of the fifth slider whose amplitude extends to 2 meters, preferably to 1.5 meters, more preferably to 1 meter, even more preferably about 80 centimeters.

According to one embodiment, the fifth guiding mechanism 13 is secured to the fourth and second second sliders by any means that one skilled in the art would find suitable such as for example screwing. Thus linear movement of the fourth slider along the at least one fourth guiding rail may ensure similar or identical linear movement of the second second slider along the at least one second guiding rail 3.1.

According to one embodiment, device comprises a second end-effector 14 secured to the fifth slider. Said end-effector may be slid or may be driven along a first axis due to the linear movement of the fifth slider and along a second axis due to linear movement of the fourth and second second sliders. Thus said end-effector may be moved or may be driven along a rectangular rehabilitation surface; said movement being preferably achieved by only two motorized guiding mechanisms and one non-motorized guiding mechanism 3.

According to one embodiment, the second guiding mechanism 3 comprises a second slider taking up the torque induced by the force applied by a subject on the end-effector 14 and thus on the fifth guiding mechanism 13, thus avoiding the need of a driving mechanism. According to said embodiment, the second second slider is similar to the first second slider. Said embodiment provides the holding of the perpendicularity between the second guiding mechanism and the fifth guiding mechanism, and especially between the at least one second guiding rail 3.1 and the at least one fifth guiding rail.

Accordingly the two end effectors 5 and 14 are driven along a large rectangular rehabilitation surface, enabling rehabilitation, monitoring and/or assessment of two limbs, preferably of two upper limbs of a subject.

According to one embodiment, the present invention also relates to a two-degree-of-freedom planar interactive device, adapted for rehabilitation, monitoring and/or assessment of the limbs of a subject, preferably of the upper limbs of a subject, and comprising the device 11 with two end-effectors as described herein.

According to one embodiment, as illustrated in FIG. 5, the rehabilitating, monitoring and/or evaluating interactive device 16 comprises the device 11 as described herein and the same functionalities as the interactive device comprising one end-effector 6.

According to one embodiment, the interactive device 6 or 16 of the present invention provides a user-friendly large rehabilitation, adapted for a large diversity of patients (from children to elderly people), "reaching" processes and proximal-to-distal rehabilitation and enabling full flexion/extension movements of the upper limbs (i.e. elbow and shoulder). According to one embodiment, the interactive device 6 or 16 of the present invention provides a large rehabilitation surface of at least 80*80 centimeters, preferably at least 1*1 meter, more preferably 1.5*1.5 meters, even more preferably 2*2 meters. According to one embodiment, the interactive device 6 or 16 of the present invention provides a large rehabilitation surface extending to about 80*80 centimeters, about 1*1 meter, about 1.5*1.5 meters, or about 2*2 meters.

End-Effector

The present invention also relates to an end-effector intended to be used with an interactive device adapted for rehabilitation, monitoring and/or assessment of the limbs of a subject, preferably of the upper limbs of a subject.

Figure 6A:
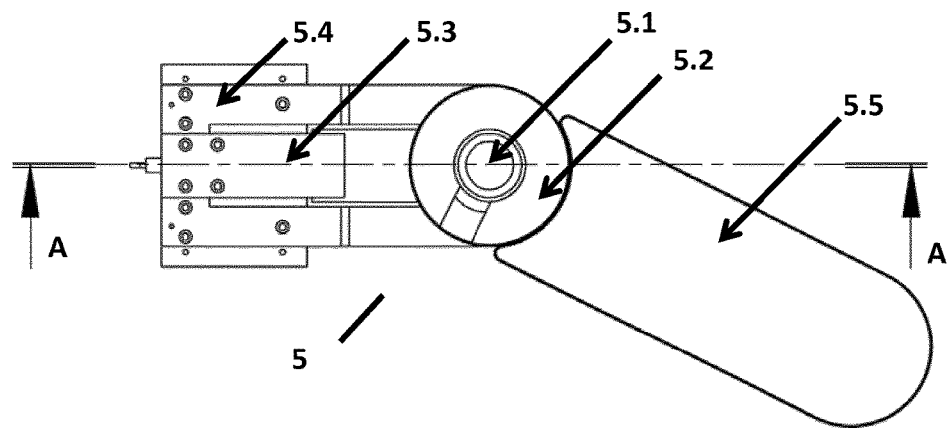
FIG. 6A is a top view of the end-effector according to an embodiment of the present invention.

Referring to the drawings, FIG. 6A illustrates the end-effector 5 comprising a handle 5.1, a hand support 5.2, a sensor part 5.3, a stopper part 5.4, and a forearm support 5.5. The handle 5.1 of the end-effector 5 is either moved by the subject and/or driven by the interactive device, thus driving the upper limb of the subject. The handle 5.1 and the forearm support 5.5 are removably connected to the hand support 5.2. The present description relates to an end-effector adapted for the upper limbs; however as it is well known from one skilled in the art, said end-effector may be adapted for other limbs.

Figure 6B:
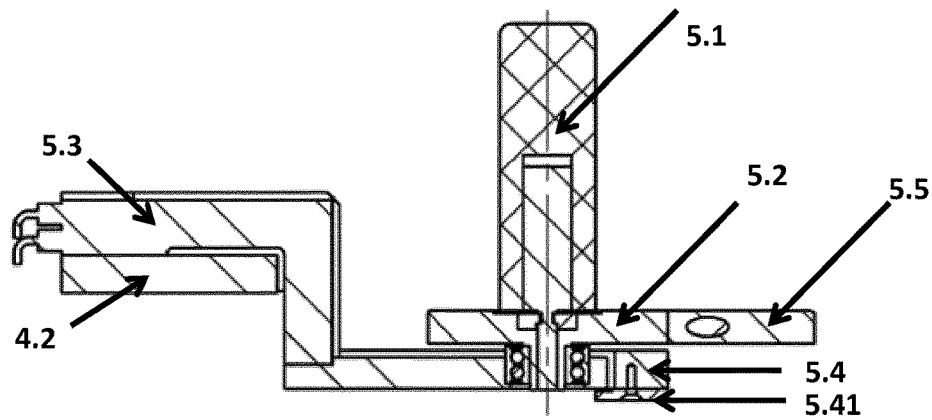
FIG. 6B is a sectional view along the A-A (cf.
Figure 7:
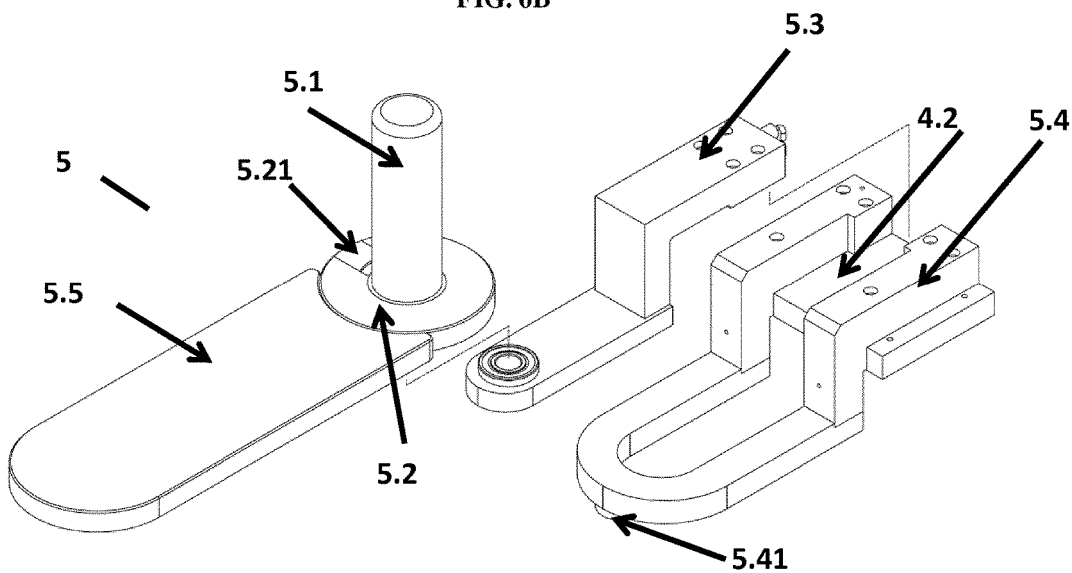
FIG. 7 is an exploded view of the end-effector according to an embodiment of the present invention.

As shown in FIGS. 6B and 7, the end-effector 5 is secured to the top side of the third slider 4.2 and the sensor part 5.3. In order to avoid exceeding the mechanical strength of the third guiding mechanism 4, especially along an axis perpendicular to the rehabilitation plane (as defined by the frontal and sagittal axis of the device), the stopper part 5.4 is secured to the top side of the third slider 4.2 and comprises a stop 5.41 adapted for contacting the work plan 10 in case of overload. According to one embodiment, the stop 5.41 may be any stop that one skilled in the art would find suitable, such as a resilient stop. Thus excessive force, especially along an axis perpendicular to the rehabilitation plane, applied on the end-effector 5 will not lead to deterioration of the third guiding mechanism 4 as the work plan 10 will take up the force through the stop 5.41 and the stopper part 5.4.

Figure 8:
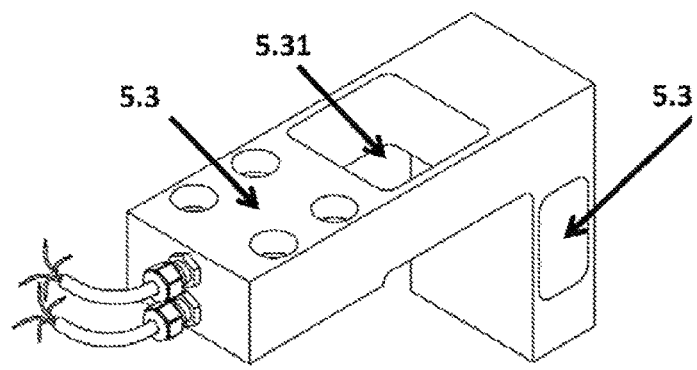
FIG. 8 is a perspective view of the sensor part of the end-effector according to an embodiment of the present invention.

The control system of the interactive device 6 requires monitoring the force between the subject and the end-effector 5. According to one embodiment, the end effector 5 comprises at least one load cell used to sense forces between the subject and the end-effector. According to the applicant locating the load cell in the handle—the point of application of the force by the subject—will advantageously avoid sensing any torque. However in such location replacement of the handle will be prevented. Thus in the present end-effector 5, the at least one load cell is located in a delocalized sensor part 5.3. Said at least one load cell of the present invention is located in at least one space 5.31 in the sensor part 5.3 (cf. FIG. 8). According to one embodiment, the at least one load cell is any load cell that one skilled in the art would find appropriate. According to one embodiment, the at least one two axes load cell of the present invention comprises for each axis four strain gauges in a Wheatstone bridge configuration in order to prevent sensing torque even in the delocalized sensor part 5.3.

As illustrated in FIG. 7, the stopper part 5.4 comprises an empty part for accommodating the sensor part 5.3. The projected surface of the stopper part 5.4 on the rehabilitation plane has indeed a U-shaped wherein the two ends of the U are connected to the third slider 4.2 and the stop 5.41 is connected to the base and wherein the sensor part 5.3 is located inside said U. According to one embodiment, the sensor part 5.3 is designed so that, in usual use, said part 5.3 is mechanically isolated from the stopper part 5.4. Thus the load cell will only sense the force along the two axis of the device 1 or interactive device 6.

According to one embodiment, hand support 5.2 is secured to the sensor part 5.3 and does not press on the stopper part 5.4 unless if excessive forces, especially along an axis perpendicular to the rehabilitation plane, are applied on the handle 5.1, the hand support 5.2 and/or the forearm support 5.5. If excessive forces are applied on the sensor part 5.3, said mechanically isolated sensor part 5.3 will press on the stopper part 5.4. In one embodiment wherein excessive forces are applied on the sensor part 5.3, the sensor part 5.3 presses on the stopper part 5.4 due to a diameter of said hand support 5.2 exceeding the width of the internal hollow space of the U-shaped stopper part 5.4. Thus in the present invention, the end-effector 5 provides an efficient way to sense forces along the two axis of the device, namely the sagittal and frontal axis and does not sense any torque, any friction forces in the rehabilitation plane or any forces in the direction perpendicular to the rehabilitation plane.

Removable Handle and Forearm Support

The present invention also relates to a removable handle and/or forearm support that can be removed from an end-effector intended to be used with an interactive device adapted for rehabilitation, monitoring and/or assessment of the limbs of a subject, preferably of the upper limbs of a subject. In the field of rehabilitation, neuro-rehabilitation, assessment and/or monitoring of the upper limbs of a subject, allowing replacement of handle to adapt said handle to different subjects (children, adults, etc.) and/or allowing the use of a forearm support is advantageous. For example, the therapist may choose, if the hand of the subject is too weak, to remove the handle for securing the forearm of the patient to the forearm support. The present description relates to a removable handle and forearm support adapted for the upper limbs of a subject; however as it is well known from one skilled in the art, said removable handle and forearm support may be adapted for other limbs.

Figure 9:
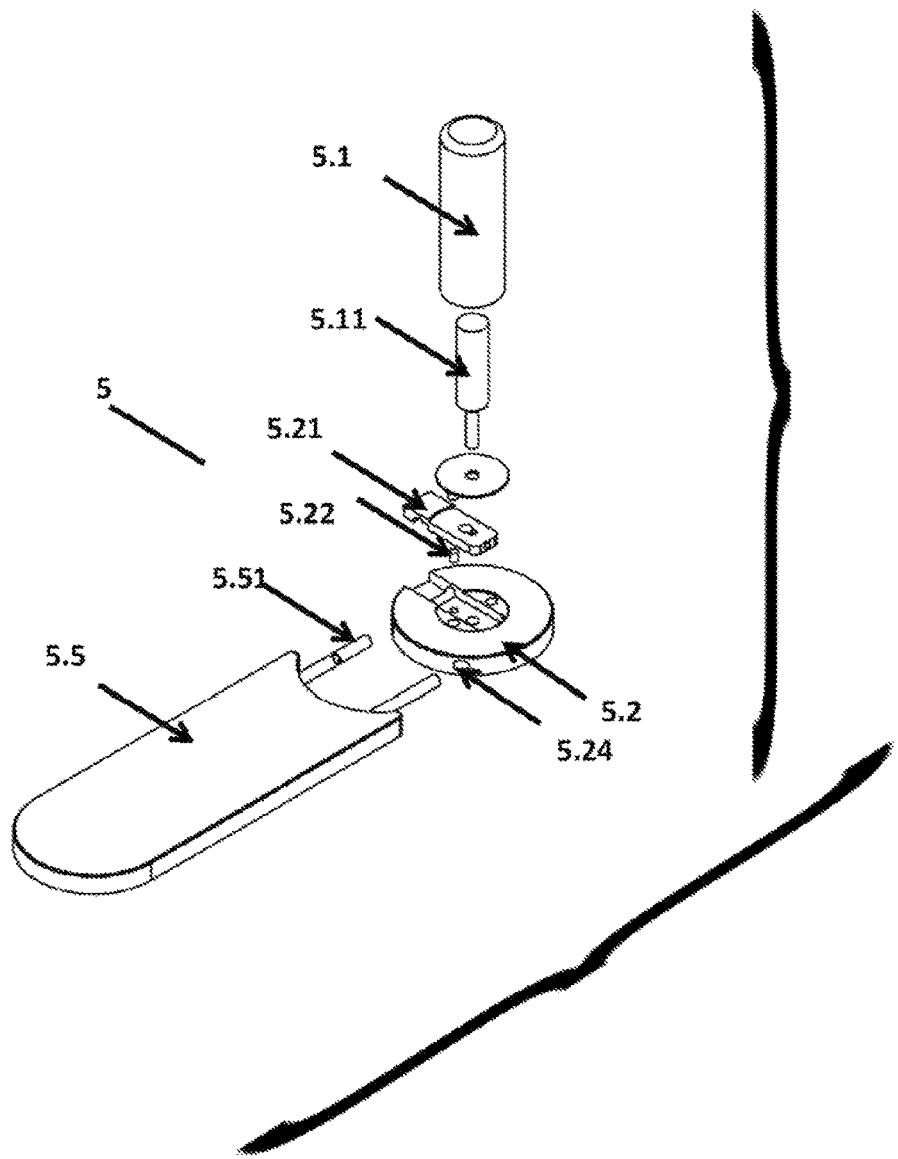
FIG. 9 is an exploded view of the handle, forearm support and hand support of the end-effector according to an embodiment of the present invention.

In order to implement removable handle and/or forearm support, the end-effector 5 of the present invention comprises, as depicted in FIG. 9, a hand support 5.2 for supporting the hand of the subject, a forearm support 5.5 for supporting the forearm of the subject and a handle 5.1. According to one embodiment, the removable handle 5.1 and the removable forearm support 5.5 are removably connected to the hand support 5.2. According to one embodiment, the hand support 5.2 is secured to the sensor part 5.3 of the end effector 5 by any means that one skilled in the art would find suitable such as for example retaining ring, snap fitting.

According to one embodiment, to achieve said removals the hand support 5.2 comprises a spring-loaded locking part 5.21. Said spring-loaded locking part 5.21 may be translated along an axis in the plane of the hand support 5.2. When pushed the locking part may be translated; subsequently the return force of the spring enables the locking part 5.21 to return to its initial position. According to one embodiment, the stroke of the spring-loaded locking part 5.21 is defined by the relative movement of a pin 5.22 protruding from the hand support 5.2 in an oblong hole 5.211 located in said locking part 5.21 (cf. FIG. 10C).

Figure 10A:
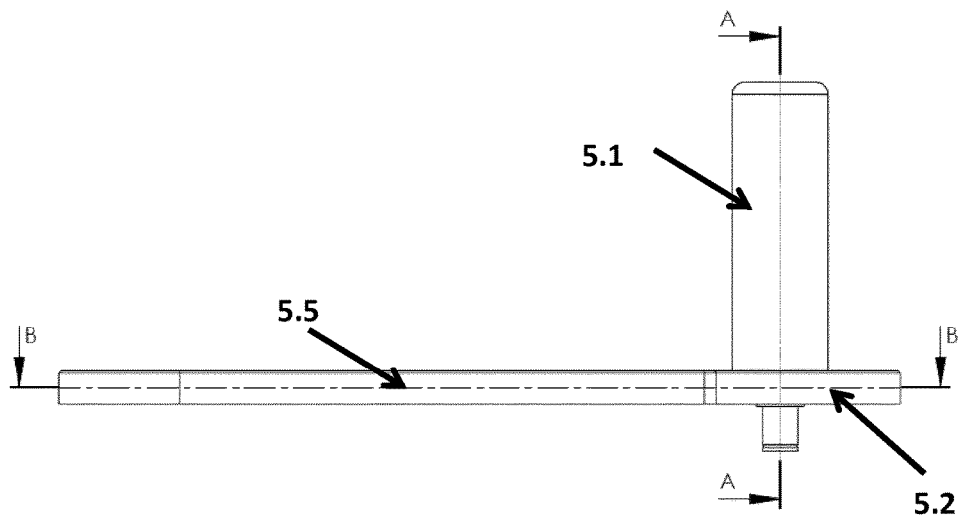
FIG. 10A is a side view of the handle, forearm support and hand support of the end-effector according to an embodiment of the present invention.
Figure 10B:
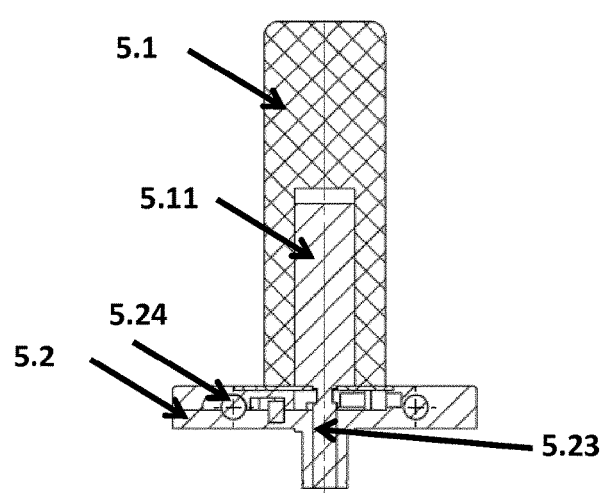
FIG. 10B is a sectional view along the A-A axis (cf.
Figure 10C:
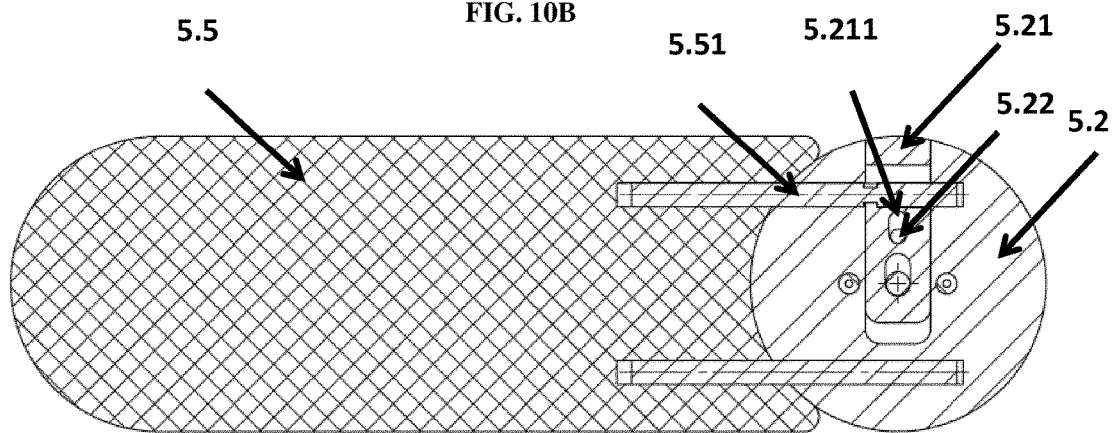
FIG. 10C is a sectional view along the B-B axis (cf.

According to one embodiment, handle 5.1 comprises a handle support 5.11 secured to the handle by any means that one skilled in the art would find suitable such as for example friction fitting or bonding (cf. FIGS. 9 and 10B).

Figure 11:
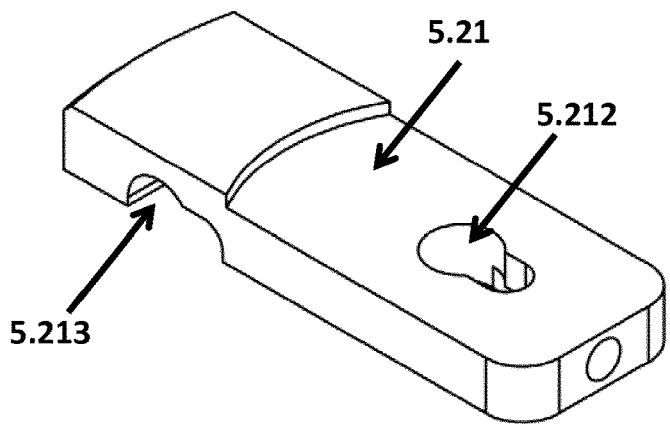
FIG. 11 is a perspective view of the locking part of the end-effector according to an embodiment of the present invention.

According to one embodiment, as illustrated in FIG. 11, the locking part 5.21 comprises a pear-shaped orifice 5.212. According to one embodiment, the handle support 5.11 comprises a rod removably connected to the hand support 5.2; said rod may be released from the hand support 5.2 by action on the locking part 5.21, thereby enabling removal of the handle 5.1. According to one embodiment, the rod of the handle support 5.11 comprises at least one circumferential groove. According to one embodiment, the rod has a diameter corresponding to the flared portion of the pear-shaped orifice 5.212 and the at least one circumferential groove has a diameter corresponding to the constricted portion of the pear-shaped orifice 5.212. According to one embodiment, the hand support 5.2 comprises a hole 5.23 designed for partly accommodating the rod of the handle support 5.11 and being either (i) aligned with the constricted portion of the pear-shaped orifice 5.212 of the locking part 5.21 when said locking part 5.21 is in its initial position or (ii) aligned with the flared portion of the pear-shaped orifice 5.212 of the locking part 5.21 when said locking part 5.21 is pushed.

By this configuration, the rod of the handle support 5.11 can easily engage the hand support 5.2 when said rod is in alignment with the flared portion of the orifice 5.212. Then by sliding of the locking part to its initial position due to the spring force, the constricted portion of the orifice 5.212 may be fitted into the groove provided on the rod of the handle support, thus firmly holding the handle 5.1 with respect to the hand support 5.2.

To separate the handle 5.1 from the hand support 5.2, the user may slide the locking part 5.21 to release the groove fitted in the constricted portion of the orifice 5.212, then the handle 5.1 may be removed by pulling.

According to one embodiment, the forearm support 5.5 comprises at least two rods 5.51, protruding from the forearm support 5.5, designed to be inserted in at least two holes 5.24 of the hand support 5.2. According to one embodiment, at least one of said rods is designed to be inserted in the hand support 5.2 and then in the locking part 5.21.

According to one embodiment, as depicted in FIG. 11, the locking part 5.21 comprises a half-pear-shaped orifice 5.213, preferably located on the side of the locking part 5.21. According to one embodiment, forearm support 5.5 comprises at least one rod 5.51 removably connected to the hand support 5.2, said at least one rod 5.51 is released from the hand support 5.2 by action on the locking part 5.21, thereby enabling removal of the forearm support 5.5. According to one embodiment, the at least one rod 5.51 of the forearm support 5.5 comprises at least one circumferential groove. According to one embodiment, the at least one rod 5.51 has a diameter corresponding to the flared portion of the half-pear-shaped orifice 5.213 and the at least one circumferential groove has a diameter corresponding to the constricted portion of the half-pear-shaped orifice 5.213. According to one embodiment, the hole 5.24 of the hand-support 5.2, designed for partly accommodating the at least one rod 5.51, is either (i) aligned with the constricted portion of the half-pear-shaped orifice 5.213 of the locking part 5.21 when said locking part 5.21 is in its initial position and (ii) aligned with the flared portion of the half-pear-shaped orifice 5.213 of the locking part 5.21 when said locking part 5.21 is pushed.

By this configuration, the at least one rod 5.51 of the forearm support 5.5 can easily engage the hand support 5.2, when said at least one rod is aligned with the flared portion of the orifice 5.213. Then by sliding of the locking part 5.21 to its initial position due to the spring force, the constricted portion of the orifice 5.213 may be fitted into the groove provided on the at least one rod 5.51 of the forearm support 5.5, thus firmly holding the forearm support 5.5 with the hand support 5.2.

To separate the forearm support 5.5 from the hand support 5.2, the user may slide the locking part 5.21 to release the groove fitted in the constricted portion of the orifice 5.213, then the forearm support 5.5 may be removed by pulling.

Thus according to an embodiment, the hand support 5.2 of the present invention, and especially the locking part 5.21, enables the removal and/or the locking of, simultaneously, the handle 5.1 and the forearm support 5.5, by action of the locking part 5.21. According to one embodiment, the hand support 5.2 comprises a spring loaded locking part 5.21 comprising two orifices 5.212, 5.213, each having a flared portion and a constricted portion. By translation of the locking part, the flared portion of the first orifice 5.212 can accommodate a rod from the handle 5.11 and the flared portion of the second orifice 5.213 can accommodate a rod from the forearm support 5.51. By back translation, the constricted portion of the first orifice 5.212 may be fitted in a circumferential groove of the rod of the handle 5.11 and the constricted portion of the second orifice 5.213 is fitted in a circumferential groove of the rod 5.51 of the forearm support 5.5, thus locking said forearm support 5.5 and said handle 5.1 with respect to the hand support 5.2. To separate the forearm support 5.5 and the handle 5.1 from the hand support 5.2, the user may slide the locking part 5.21 to release the grooves fitted in the constricted portions of the orifices 5.212 and 5.213, then the forearm support 5.5 and the handle 5.1 may be removed.

While various embodiments have been described and illustrated, the detailed description is not to be construed as being limited hereto. Various modifications can be made to the embodiments by those skilled in the art without departing from the true spirit and scope of the disclosure as defined by the claims.

The invention claimed is:

1. A two-degree-of-freedom planar rehabilitating, monitoring and/or evaluating device, comprising:
   a first guiding mechanism,
   a second guiding mechanism, substantially parallel to the first guiding mechanism,
   a third guiding mechanism, substantially perpendicular to the first and second guiding mechanisms, and
   an end-effector,
   wherein the third guiding mechanism is connected to the first and second guiding mechanisms, the end-effector is connected to the third guiding mechanism; and
   wherein:
   the first guiding mechanism comprises at least one first guiding rail, a first slider slidably connected to the at least one first guiding rail and a first driving module driving the first slider;
   the second guiding mechanism comprises at least one second guiding rail, a second slider slidably connected to the at least one second guiding rail;
   the third guiding mechanism comprises at least one third guiding rail, a third slider slidably connected to the at least one third guiding rail and a third driving module driving the third slider; and
   wherein the second guiding mechanism does not comprise any driving module.

2. The two-degree-of-freedom planar rehabilitating, monitoring and/or evaluating device according to claim 1, wherein the third guiding mechanism is connected to the first and second guiding mechanisms through the first and second sliders.

3. The two-degree-of-freedom planar rehabilitating, monitoring and/or evaluating device according to claim 1, wherein the end-effector is connected to the third slider.

4. The two-degree-of-freedom planar rehabilitating, monitoring and/or evaluating device according to claim 1, wherein the end-effector may be driven by the driving modules along a first axis defined by the at least one third guiding rail and along a second axis defined by the at least one first guiding rail.

5. The two-degree-of-freedom planar rehabilitating, monitoring and/or evaluating device according to claim 1, wherein the at least one first, second and/or third guiding rails allow a linear movement of the first, second and/or third sliders whose amplitude extends to 2 meters.

6. The two-degree-of-freedom planar rehabilitating, monitoring and/or evaluating device according to claim 1, wherein the second slider takes-up the torque induced by the force applied by a subject on the third guiding mechanism.

7. The two-degree-of-freedom planar rehabilitating, monitoring and/or evaluating device according to claim 1, wherein the second slider comprises a main body and at least one bearing part protruding downwards from the main body, wherein said at least one bearing part is slidably connected to the at least one second guiding rail and wherein the length, along the axis of the at least one second guiding rail, of said at least one bearing part between the two bearing points located at the opposite ends is at least 10 centimeters.

8. The two-degree-of-freedom planar rehabilitating, monitoring and/or evaluating device according to claim 7, wherein the second slider comprises a main body and two bearing parts protruding downwards from the main body, wherein said first and second bearing parts are slidably connected to the at least one second guiding rail and wherein said first and second bearing are spaced, along the axis of the at least one second guiding rail, by at least 10 centimeters.

9. The two-degree-of-freedom planar rehabilitating, monitoring and/or evaluating device according to claim 1, wherein the first slider and the third slider are connected respectively to the at least one first guiding rail and the at least one third guiding rail through bearings; and wherein the second slider is connected to the at least one second guiding rail through at least one bearing.

10. The two-degree-of-freedom planar rehabilitating, monitoring and/or evaluating device according to claim 1, further comprising:
a fourth guiding mechanism, substantially parallel to the first and second guiding mechanisms,
a fifth guiding mechanism, substantially parallel to the third guiding mechanism and substantially perpendicular to the first, second and fourth guiding mechanisms,
a second end-effector,
wherein the fifth guiding mechanism is connected to the second and fourth guiding mechanisms, and
wherein the end-effector is connected to the fifth guiding mechanism.

11. A two-degree-of-freedom planar rehabilitating, monitoring and/or evaluating interactive device adapted for rehabilitation, monitoring and assessment of the limbs, of a subject, comprising:
a two-degree-of-freedom planar rehabilitation device comprising:
a first guiding mechanism,
a second guiding mechanism, substantially parallel to the first guiding mechanism,
a third guiding mechanism, substantially perpendicular to the first and second guiding mechanisms, and
an end-effector,
wherein the third guiding mechanism is connected to the first and second guiding mechanisms, the end-effector is connected to the third guiding mechanism and wherein:
the first guiding mechanism comprises at least one first guiding rail, a first slider slidably connected to the at least one first guiding rail and a first driving module driving the first slider;
the second guiding mechanism comprises at least one second guiding rail, a second slider slidably connected to the at least one second guiding rail;
the third guiding mechanism comprises at least one third guiding rail, a third slider slidably connected to the at least one third guiding rail and a third driving module driving the third slider; and
wherein the second guiding mechanism does not comprise any driving module;
further comprising a control system controlling the motion of said interactive device.

12. The two-degree-of-freedom planar rehabilitating, monitoring and/or evaluating interactive device according to claim 11, wherein the device is arranged on a chassis and the interactive device comprises a display for interaction with the subject, at least one force sensor located in the end-effector and at least one position sensor located in the driving modules.

13. The two-degree-of-freedom planar rehabilitating, monitoring and/or evaluating interactive device according to claim 12, wherein the device is further comprising a work plan.

14. The two-degree-of-freedom planar rehabilitating, monitoring and/or evaluating interactive device according to claim 11, wherein the interactive device may be operated in three control modes defining the interaction between the subject and the interactive device: a passive mode, wherein the interactive device guides movements of a limb of the subject along a predefined path; an active mode, wherein the interactive device does not provide incentives to the subject and only controls the movements carried out by the subject and an active-passive mode, wherein the interactive device assists the movement of a limb of the subject depending on the motor skills of the subject.

15. The two-degree-of-freedom planar rehabilitating, monitoring and/or evaluating interactive device according to claim 14, wherein depending on the motor skills of the subject, the control system regulates in real-time the lateral interaction force, preventing the subject to deviate from a predefined path, the longitudinal interaction force, assisting the subject to move along the predefined path at a predefined speed, and the initiation time after which the interactive device initiates a movement if no movement has been started by the subject.

16. The two-degree-of-freedom planar rehabilitating, monitoring and/or evaluating interactive device according to claim 11, wherein the interactive device further comprises user-friendly graphical environment displayed on the display and contextualized as tasks or games.

* * * * *